United States Patent
Altshuler et al.

(10) Patent No.: US 6,605,080 B1
(45) Date of Patent: *Aug. 12, 2003

(54) METHOD AND APPARATUS FOR THE SELECTIVE TARGETING OF LIPID-RICH TISSUES

(75) Inventors: Gregory B. Altshuler, Wilmington, MA (US); R. Rox Anderson, Lexington, MA (US); Dieter Manstein, Boston, MA (US)

(73) Assignees: The General Hospital Corporation, Boston, MA (US); Palomar Medical Technologies, Inc., Burlington, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/277,307
(22) Filed: Mar. 26, 1999

Related U.S. Application Data

(60) Provisional application No. 60/079,710, filed on Mar. 27, 1998.

(51) Int. Cl.[7] .............................. A61B 18/18
(52) U.S. Cl. .................. 606/3; 606/13; 606/89
(58) Field of Search ................ 606/2–4, 7–11, 606/13–17, 1; 607/88, 89, 96, 100–101, 113; 250/358.1

(56) References Cited

U.S. PATENT DOCUMENTS

| | | |
|---|---|---|
| 3,327,712 A | 6/1967 | Kaufman et al. |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |

(List continued on next page.)

FOREIGN PATENT DOCUMENTS

| | | |
|---|---|---|
| AT | 400305 B | 4/1995 |
| DE | 3837248 A1 | 5/1990 |
| EP | 0142671 A1 | 5/1985 |
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0755698 A2 | 1/1997 |
| EP | 0763371 A2 | 3/1997 |
| EP | 0765673 A2 | 4/1997 |
| EP | 0765674 A2 | 4/1997 |

(List continued on next page.)

OTHER PUBLICATIONS

G.B. Altshuler et al., "Acoustic response of hard dental tissues to pulsed laser action," SPIE, vol. 2080, Dental Application of Lasers, pp. 97–103, 1993.

G.B. Altshuler et al., "Extended theory of selective photothermolysis," Lasers in Surgery and Medicine, vol. 29, pp. 416–432, 2001.

R.L. Amy & R. Storb, "Selective mitochondrial damage by a ruby laser microbeam: An electron microscopic study," Science, vol. 15, pp. 756–758, Nov. 1965.

(List continued on next page.)

*Primary Examiner*—Michael Peffley
(74) *Attorney, Agent, or Firm*—Wolf, Greenfield & Sacks, P.C.

(57) ABSTRACT

A method and apparatus are provided for targeting lipid-rich tissue to effect a desired, the method/apparatus involving irradiating the lipid-rich tissue with energy at a wavelength preferentially absorbed by lipid cells, such wavelength being preferably in a band between 880 nm and 935 nm, 1150 nm and 1230 nm, 1690 nm to 1780 nm, or 2250 nm to 2450 nm with a fluence and duration sufficient to achieve a desired treatment. For preferred embodiments, the irradiation wavelength is between 900–930 nm, 1190–1220 nm, 1700–1730 nm, or 2280–2350 nm. The method and apparatus may for example be used to target one or more sebaceous glands for the treatment of acne or hair removal, to target subcutaneous fat for removal thereof or for targeting fat on anatomical elements for various purposes.

72 Claims, 4 Drawing Sheets

U.S. PATENT DOCUMENTS

| | | | |
|---|---|---|---|
| 3,818,914 A | | 6/1974 | Bender |
| 3,834,391 A | | 9/1974 | Block |
| 3,900,034 A | | 8/1975 | Katz et al. |
| 4,233,493 A | | 11/1980 | Nath |
| 4,273,109 A | | 6/1981 | Enderby |
| 4,316,467 A | | 2/1982 | Muckerheide |
| 4,388,924 A | | 6/1983 | Weissman et al. |
| 4,461,294 A | | 7/1984 | Baron |
| 4,539,987 A | | 9/1985 | Nath et al. |
| 4,608,978 A | | 9/1986 | Rohr |
| 4,617,926 A | | 10/1986 | Sutton |
| 4,695,697 A | | 9/1987 | Kosa |
| 4,718,416 A | | 1/1988 | Nanaumi |
| 4,733,660 A | | 3/1988 | Itzkan |
| 4,747,660 A | | 5/1988 | Nishioka et al. |
| 4,819,669 A | | 4/1989 | Politzer |
| 4,832,024 A | | 5/1989 | Boussignac et al. |
| 4,860,172 A | | 8/1989 | Schlager et al. |
| 4,860,744 A | | 8/1989 | Johnson et al. |
| 4,917,084 A | * | 4/1990 | Sinofsky .................. 606/7 |
| 4,926,227 A | | 5/1990 | Jensen |
| 4,945,239 A | * | 7/1990 | Wist et al. ............... 250/358.1 |
| 5,000,752 A | | 3/1991 | Hoskin et al. |
| 5,057,104 A | | 10/1991 | Chess |
| 5,059,192 A | | 10/1991 | Zaias |
| 5,065,515 A | | 11/1991 | Iderosa |
| 5,071,417 A | | 12/1991 | Sinofsky |
| 5,108,388 A | | 4/1992 | Trokel |
| 5,137,530 A | | 8/1992 | Sand |
| 5,140,984 A | | 8/1992 | Dew et al. |
| 5,178,617 A | | 1/1993 | Kuizenga et al. |
| 5,182,557 A | | 1/1993 | Lang |
| 5,182,857 A | | 2/1993 | Simon |
| 5,196,004 A | * | 3/1993 | Sinofsky .................. 606/3 |
| 5,207,671 A | | 5/1993 | Franken et al. |
| 5,225,926 A | | 7/1993 | Cuomo et al. |
| 5,226,907 A | | 7/1993 | Tankovich |
| 5,282,797 A | | 2/1994 | Chess |
| 5,300,097 A | | 4/1994 | Lerner et al. |
| 5,304,170 A | | 4/1994 | Green |
| 5,306,274 A | | 4/1994 | Long |
| 5,320,618 A | | 6/1994 | Gustafsson |
| 5,334,191 A | | 8/1994 | Poppas et al. |
| 5,334,193 A | | 8/1994 | Nardella |
| 5,344,418 A | | 9/1994 | Ghaffari |
| 5,348,551 A | | 9/1994 | Spears et al. |
| 5,350,376 A | | 9/1994 | Brown |
| 5,380,317 A | | 1/1995 | Everett et al. |
| 5,403,306 A | | 4/1995 | Edwards et al. |
| 5,405,368 A | | 4/1995 | Eckhouse |
| 5,415,654 A | | 5/1995 | Daikuzono |
| 5,425,728 A | | 6/1995 | Tankovich |
| 5,474,549 A | | 12/1995 | Ortiz et al. |
| 5,486,172 A | | 1/1996 | Chess |
| 5,505,726 A | | 4/1996 | Meserol |
| 5,505,727 A | | 4/1996 | Keller |
| 5,519,534 A | | 5/1996 | Smith et al. |
| 5,578,866 A | | 11/1996 | DePoorter et al. |
| 5,595,568 A | | 1/1997 | Anderson et al. |
| 5,616,140 A | | 4/1997 | Prescott |
| 5,620,478 A | | 4/1997 | Eckhouse |
| 5,626,631 A | | 5/1997 | Eckhouse |
| 5,630,811 A | | 5/1997 | Miller |
| 5,649,972 A | | 7/1997 | Hochstein |
| 5,655,547 A | | 8/1997 | Karni |
| 5,662,643 A | | 9/1997 | Kung et al. |
| 5,662,644 A | | 9/1997 | Swor |
| 5,683,380 A | * | 11/1997 | Eckhouse et al. ............ 606/9 |
| 5,698,866 A | | 12/1997 | Doiron et al. |
| 5,735,844 A | | 4/1998 | Anderson et al. |
| 5,735,884 A | | 4/1998 | Thompson et al. |
| 5,743,901 A | | 4/1998 | Grove et al. |
| 5,755,751 A | | 5/1998 | Eckhouse |
| 5,759,200 A | | 6/1998 | Azar |
| 5,782,249 A | | 7/1998 | Weber et al. |
| 5,810,801 A | | 9/1998 | Anderson et al. |
| 5,817,089 A | | 10/1998 | Tankovich et al. |
| 5,820,625 A | | 10/1998 | Izawa et al. |
| 5,820,626 A | | 10/1998 | Baumgardner |
| 5,824,023 A | | 10/1998 | Anderson |
| 5,828,803 A | | 10/1998 | Eckhouse |
| 5,830,208 A | | 11/1998 | Muller |
| 5,836,999 A | | 11/1998 | Eckhouse et al. |
| 5,849,029 A | | 12/1998 | Eckhouse et al. |
| 5,853,407 A | * | 12/1998 | Miller ..................... 606/9 |
| 5,885,211 A | | 3/1999 | Eppstein et al. |
| 5,885,273 A | | 3/1999 | Eckhouse et al. |
| 5,885,274 A | | 3/1999 | Fullmer et al. |
| 5,944,748 A | | 8/1999 | Mager et al. |
| 5,948,011 A | | 9/1999 | Knowlton |
| 5,954,710 A | * | 9/1999 | Paolini et al. .............. 606/7 |
| 5,964,749 A | | 10/1999 | Eckhouse et al. |
| 5,968,033 A | | 10/1999 | Fuller et al. |
| 5,968,034 A | | 10/1999 | Fullmer et al. |
| 6,015,404 A | | 1/2000 | Altshuler et al. |
| 6,027,495 A | | 2/2000 | Miller |
| RE36,634 E | | 3/2000 | Ghaffari |
| 6,050,990 A | | 4/2000 | Tankovich et al. |
| 6,056,738 A | | 5/2000 | Marchitto et al. |
| 6,059,820 A | | 5/2000 | Baronov |
| 6,096,029 A | | 5/2000 | O'Donnell, Jr. |
| 6,074,382 A | | 6/2000 | Asah et al. |
| 6,080,146 A | * | 6/2000 | Altshuler et al. ............ 606/9 |
| 6,096,209 A | | 8/2000 | O'Brien et al. |
| 6,104,959 A | | 8/2000 | Spertell |
| 6,120,497 A | | 9/2000 | Anderson et al. |
| 6,149,644 A | * | 11/2000 | Xie ........................ 606/9 |
| 6,174,325 B1 | | 1/2001 | Eckhouse |
| 6,197,020 B1 | | 3/2001 | O'Donnell |
| 6,235,016 B1 | | 5/2001 | Stewart |
| 6,273,884 B1 | | 8/2001 | Altshuler et al. |
| 6,273,885 B1 | | 8/2001 | Koop et al. |
| 6,280,438 B1 | | 8/2001 | Eckhouse et al. |

FOREIGN PATENT DOCUMENTS

| | | |
|---|---|---|
| EP | 0783904 A2 | 7/1997 |
| EP | 1038505 A2 | 9/2000 |
| FR | 2591902 | 6/1987 |
| GB | 2044908 A | 10/1980 |
| GB | 2123287 A | 2/1984 |
| GB | 2360946 A | 10/2001 |
| RU | 2082337 C1 | 6/1997 |
| RU | 2089126 C1 | 10/1997 |
| RU | 2089127 C1 | 10/1997 |
| RU | 2096051 C1 | 11/1997 |
| RU | 2122848 C1 | 10/1998 |
| WO | WO 86/02783 | 5/1986 |
| WO | WO 90/00420 | 1/1990 |
| WO | WO 92/16338 | 1/1992 |
| WO | WO 92/19165 | 11/1992 |
| WO | WO 93/05920 | 4/1993 |
| WO | WO 95/15725 | 6/1995 |
| WO | WO 95/32441 | 11/1995 |
| WO | WO 96/23447 | 8/1996 |
| WO | WO 96/25979 | 8/1996 |
| WO | WO 97/13458 | 4/1997 |
| WO | WO 98/04317 | 2/1998 |
| WO | WO 98/24507 | 6/1998 |
| WO | WO 98/51235 | 11/1998 |
| WO | WO 98/52481 | 11/1998 |
| WO | WO 99/27997 A1 | 6/1999 |

| | | |
|---|---|---|
| WO | WO 99/29243 | 6/1999 |
| WO | WO 99/38569 | 8/1999 |
| WO | WO 99/46005 | 9/1999 |
| WO | WO 99/49937 A1 | 10/1999 |
| WO | WO 00/03257 A1 | 1/2000 |
| WO | WO 00/71045 A1 | 11/2000 |
| WO | WO 00/74781 A1 | 12/2000 |
| WO | WO 00/78242 A1 | 12/2000 |
| WO | WO 01/03257 A1 | 1/2001 |
| WO | WO 01/34048 A1 | 5/2001 |
| WO | WO 01/42671 A1 | 6/2001 |
| WO | WO 01/54606 A1 | 8/2001 |
| WO | WO 02/53050 A1 | 7/2002 |

OTHER PUBLICATIONS

R.R. Anderson et al., "The optics of human skin," Journal of Investigative Dermatology, vol. 77, No. 1, pp. 13–19, 1981.

R.R. Anderson & J.A. Parrish, "Selective photothermolysis: Precise microsurgery by selective absorption of pulsed radiation," Science, vol. 220, pp. 524–527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109–116, Sep. 1995.

J.S. Dover et al., "Pigmented guinea pig skin irradiated with Q–switched ruby laser pulses," Arch Dermatol, vol. 125, pp. 43–49, Jan. 1989.

L.H. Finkelstein & L.M. Blatstein, "Epilation of hair–bearing urethral grafts using the neodymium:yag surgical laser," Journal of Urology, vol. 146, pp. 840–842, Sep. 1991.

L. Goldman, Biomedical Aspects of the Laser, Springer–Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S–92–S–93, Jan.–Feb. 1965.

L. Goldman, "Effects of new laser systems on the skin," Arch Dermatol., vol. 108, pp. 385–390, Sep. 1973.

L. Goldman, "Laser surgery for skin cancer," New York State Journal of Medicine, pp. 1897–1900, Oct. 1977.

L. Goldman, "Surgery by laser for malignant melanoma," J. Dermatol. Surg. Oncol., vol. 5, No. 2, pp. 141–144, Feb. 1979.

L. Goldman, "The skin," Arch Environ Health, vol. 18, pp. 434–436, Mar. 1969.

L. Goldman & D.F. Richfield, "The effect of repeated exposures to laser beams," Acta derm.–vernereol., vol. 44, pp. 264–268, 1964.

L. Goldman & R.J. Rockwell, "Laser action at the cellular level," JAMA, vol. 198, No. 6, pp. 641–644, Nov. 1966.

L. Goldman & R.G. Wilson, "Treatment of basal cell epithelioma by laser radiation," JAMA, vol. 189, No. 10, pp. 773–775.

L. Goldman et al., The biomedical aspects of lasers, JAMA, vol. 188, No. 3, pp. 302–306, Apr. 1964.

L. Goldman et al., "Effect of the laser beam on the skin, Preliminary report" Journal of Investigative Dermatology, vol. 40, pp. 121–122, 1963.

L. Goldman et al., "Effect of the laser beam on the skin, III. Exposure of cytological preparations," Journal of Investigative Dermatology, vol. 42, pp. 247–251, 1964.

L. Goldman et al., "Impact of the laser on nevi and melanomas," Archives of Dermatology, vol. 90, pp. 71–75, Jul. 1964.

L. Goldman et al., "Laser treatment of tattoos, A preliminary survey of three year's clinical experience," JAMA, vol. 201, No. 11, pp. 841–844, Sep. 1967.

L. Goldman et al., "Long–term laser exposure of a senile freckle, " ArchEnviron Health, vol. 22, pp. 401–403, Mar. 1971.

L. Goldman et al., "Pathology, Pathology of the effect of the laser beam on the skin," Nature, vol. 197, No. 4870, pp. 912–914, Mar. 1963.

L. Goldman et al., "Preliminary investigation of fat embolization from pulsed ruby laser impacts of bone," Nature, vol. 221, pp. 361–363, Jan. 1969.

L. Goldman et al., "Radiation from a Q–switched ruby laser, Effect of repeated impacts of power output of 10 megawatts on a tattoo of man, " Journal of Investigative Dermatology, vol. 44, pp. 69–71, 1965.

L. Goldman et al., "Replica microscopy and scanning electron microscopy of laser impacts on the skin," Journal of Investigative Dermatology, vol. 52, No. 1, pp. 18–24, 1969.

M.C. Grossman et al., "Damage to hair follicles by normal–mode ruby laser pulses," Journal of the American Academy of Dermatology, vol. 35, No. 6, pp. 889–894, Dec. 1996.

E. Klein et al., "Biological effects of laser radiation 1.," Northeast Electroncis Research and Engineering Meeting, NEREM Record, IEEE catalogue No. F–60, pp. 108–109, 1965.

J.G. Kuhns et al., "Laser injury in skin," Laboratory Investigation, vol. 17, No. 1, pp. 1–13, Jul. 1967.

J.G. Kuhns et al., "Biological effects of laser radiation II Effects of laser irradiation on the skin, " NEREM Record, pp. 152–153, 1965.

R.J. Margolis et al., "Visible action spectrum for melanin-–specific selective photothermolysis," Lasers in Surgery and Medicine, vol. 9, pp. 389–397, 1989.

J.A. Parrish, "Selective thermal effects with pulsed irradiation from lasers: From organ to organelle," Journal of Investigative Dermatology, vol. 80, No. 6 Supplement, pp. 75s–80s, 1983.

L. Polla et al., "Melanosomes are a primary target of Q–switched ruby laser irradiation in guinea pig skin," Journal of Investigative Dermatology, vol. 89, No. 3, pp. 281–286, Sep. 1987.

T. Shimbashi & T. Kojima, "Ruby laser treatment of pigmented skin lesions," Aesth. Plast. Surg., vol. 19, pp. 225–229, 1995.

Stratton, K., et al., "Biological Effects of Laser Radiation II: ESR Studies of Melanin Containing Tissues after Laser Irradiation," Northeast Electronics Research and Engineering Meeting –NEREM Record, IEEE Catalogue No. F–60, pp. 150–151, Nov. 1965.

C.R. Taylor et al., "Treatment of tattoos by Q–switched ruby laser," Arch. Dermatol. vol. 126, pp. 893–899, Jul. 1990.

V.V. Tuchin, "Laser light scattering in biomedical diagnostics and therapy," Journal of Laser Applications, vol. 5, No. 2–3, pp. 43–60, 1993.

S. Watanabe et al, "Comparative studies of femtosecond to microsecond laser pulses on selective pigmented cell injury in skin," Photochemistry and Photobiology, vol. 53, No. 6, pp. 757–762, 1991.

A.J. Welch et al., "Evaluation of cooling techniques for the protection of the pidermis during HD–yag laser irradiation of the skin," Neodymium–Yag Laser in Medicine and Surgery, Elsevier Science Publishing Co., publisher, pp. 195–204, 1983.

R.B. Yules et al., "The effect of Q–switched ruby laser radiation on dermal tattoo pigment in man," Arch Surg, vol. 95, pp. 179–180, Aug. 1967.

G.G. Riggle et al., "Laser effects on normal and tumor tissue," Laser Applications in Medicine and Biology, vol. I, M.L. Wolbarsht, editor, Plenum Press, publishers, Chapter 3, pp. 35–65, 1971.

Abstracts Nos. 17–19, Lasers in Surgery and Medicine, ASLMS, Supplement 13, 2001.

Abstracts Nos. 219–223, ASLMS.

Abstracts, various.

Invention description to certificate of authorship, No. 532304, "The way of investigation of radiation time structure of optical quantum generator".

Invention description to certificate of authorship, No. 719439, "The ring resonator of optical quantum generator".

Invention description of certificate of authorship, No. 741747, "The modulator of optical radiation intensity".

Invention description to certificate of authorship, No. SU 1257475 A1, "Laser interferometric device to determine no–linearity of an index of refraction of optical medium".

Invention description to certificate of authorship, No. SU 1326962 A1, "The way of determination of non–linearity of an index of refraction of optical medium".

* cited by examiner

METHOD AND APPARATUS FOR THE SELECTIVE TARGETING OF LIPID-RICH TISSUES

RELATED APPLICATIONS

This application claims priority from provisional specification 60/079710 filed Mar. 27, 1998, the subject matter of which is incorporated herein by reference.

FIELD OF THE INVENTION

This invention relates to methods and apparatus for the selective heating of lipid-rich tissue including sebaceous glands, subcutaneous fat, lipid in membranes of cells, and fat surrounding organs, vessels, hair bulbs, and other anatomical elements, and/or to the selective destruction or removal of such tissue and/or structures adjacent thereto; and more particularly to methods and apparatus for using optical radiation in selected wavebands, which radiation may be obtained from a laser or other suitable light source, to effect such heating, removal and/or destruction.

BACKGROUND OF THE INVENTION

Adipose or lipid-rich tissue, which is also sometimes referred to as "fat" or "fatty tissue", is a common cosmetic and surgical problem, and excessive body fat may also pose certain other health risks. Many factors, including heredity, glandular function, nutrition and lifestyle affect both the extent and location of body fat. Despite dieting and exercise, many people cannot lose fat, particularly in certain areas. Heretofore, liposuction, a procedure in which fat is removed by a suction cannula under local anesthesia, or other forms of fat excision have been used. Fat also occurs in pads on the face and neck and small area local liposuction has sometimes been performed in these areas. However, liposuction is an invasive surgical procedure and presents all of the disadvantages and risks to the patient involved in such a procedure, including scars at the sites of entry into skin. Another problem with liposuction is that it is not selective in only removing unwanted fat, but also rips out tissue in the path of the liposuction hose, including the collagen supporting structure holding the patient's skin in place. This can result in cosmetically unattractive sagging skin in the treated area, in addition to significant pain to the patient both during and after the procedure, risk of infection and other potential problems. The trauma caused by extreme liposuction has in some cases even resulted in the death of the patient. Further, while liposuction can be used for the removal of deep fat, it is significantly less effective for removing fat at a superficial level of subcutaneous fat just below the dermis. Such removal is desirable in some cases because it is less traumatic to the patient. However, it is difficult to do with a liposuction cannula without scratching the dermis, damage to the dermis not healing readily, and attempts to perform surface liposuction also result in an uneven removal of fat which leaves an esthetically unattractive patterning on the patient's skin. Therefore, while liposuction is still used extensively for the removal of excess fat, it is not a desirable procedure.

Fat is also a problem in various surgical procedures where it may be difficult to locate vessels, organs or other anatomical elements on which surgery is to be performed when these elements are covered in fat, and it may be difficult to close surgical openings in such elements. Performing surgery on vessels, organs or other elements covered by fat is therefore risky and current procedures for removing such fat to facilitate surgical procedures have significant limitations. Of particular concern is mesenteric fat which is a common hindrance in laparoscopic surgery. With the current trend of making surgical procedures less invasive by inserting tools through a small surgical opening, the removal of fat in the region where a surgical procedure is being performed, utilizing a tool consistent with such surgical procedures, so as to facilitate remote viewing of the anatomical element being treated/operated on is therefore becoming increasingly important.

In addition, a major problem for teenagers and others is acne which originates at least in part from obstruction of outflow from a sebaceous gland. Certain drug treatments for acne operate through a mechanism of decreasing sebaceous gland output. Destruction, removal, or unblocking of the sebaceous gland, which gland contains lipid-rich tissue, in a non-invasive manner are therefore desirable alternatives for treatment or prevention of acne.

Another related problem is the removal of unwanted hair, and in particular the long-term or permanent removal of such hair by the damage or destruction of the hair follicle. Many techniques have been employed over the years for this treatment, including electrolysis, waxing and treatments with various forms of radiation, including light. However, electrolysis is slow and both electrolysis and waxing are painful to the patient and seldom permanent. Various radiation treatments, particularly those involving light, work more effectively for patients having darker hair than for patients with light hair and various proposals have been made over the years to add a chromophore in some way to the follicle to facilitate such treatments. The use of such artificial chromphores has not heretofore been particularly successful.

Other related problems involve either removing fat, for example in the stratum corneum, under certain conditions, for example when a pressure injection is to be given, selectively porating cells having lipid-rich walls to permit substances, for example therapeutic agents, to enter the cells or to permit the removal of wanted or unwanted substances therefrom or to otherwise heat or destroy lipid-rich tissue for various therapeutic purposes.

While lasers or other light sources have been proposed in the past for heating, removal, destruction (for example killing), photocoagulation, eradication or otherwise treating (hereinafter collectively referred to as "treating" or "treatment") of lipid-rich tissue such as subcutaneous fat, the lasers proposed for such procedures have operated at a wavelength where lipid-rich tissue has an absorption coefficient which is generally significantly less then than that for water. This presents several problems. First, lipid-rich tissue is radiation heated as a result of absorption in the tissue of radiation energy. Therefore, for wavelengths at which lipid-rich tissue does not absorb the radiation strongly, large amounts of energy must be applied to the tissue in order to obtain the requisite heating. However, in addition to significantly increasing the cost of the procedure, the need for high energy poses a danger of damage to surrounding tissue or the tissue through which the radiation passes, particularly since most such tissue is primarily composed of water which absorbs the radiant energy much more at these wavelengths.

This is a particular problem for subcutaneous fat which generally starts at a depth of at least 1 to 4 mm into a patient's skin, and may be deeper for some individuals or some body areas. Therefore, in order for the radiation to target to the subcutaneous fat to cause selective heating or destruction thereof, it must pass through several millimeters of tissue formed primarily of water. Since water preferentially absorbs at these wavelengths, most of the incident radiation is absorbed in the skin prior to reaching the subcutaneous fat and, since skin is a scattering medium, incident light is also scattered and reflected from the patient's skin, resulting in a very small fraction of the incident light reaching the subcutaneous fat. Therefore, due to both the small fraction of the applied energy reaching the subcutaneous fat and the low absorption of this energy by the fat, in order to get enough energy to the subcutaneous fat at these wavelengths to be effective, large amounts of radiation would need to be applied to the overlying epidermis and dermis. Since such high levels of radiation absorbed in the dermis or epidermis would cause significant thermal damage to these skin layers at the prior art wavelengths, treatment/destruction of fat cannot be performed through the skin, but must be performed by providing an opening, for example a surgical opening, through the skin to provide direct contact with the fat tissue to be treated. Even when the radiation is applied directly to the fat tissue to be treated, high energy is required and great care must be exercised to avoid excessive radiation of surrounding or underlying tissue so as to minimize damage thereto. Other prior art fat treatment techniques, involving the use of either microwaves or ultrasound, either alone or in conjunction with liposuction, to melt or loosen the fat and to remove it or have it absorbed into the body, have either proved not to be effective for fat removal, have posed potential health hazards to patients, either actual or perceived, or have still involved invasive procedures, the risk of which have been discussed earlier.

A need therefore exists for an improved technique for heating and destroying, or otherwise targeting lipid-rich tissue, including, but not limited to, subcutaneous fat, sebaceous gland, lipid in membrane cells and fat covering anatomical elements on which surgical or other procedures are is to be performed, which does not suffer the limitations of prior art techniques, including liposuction, and which is significantly more selective than the prior art in the destruction of lipid-rich tissue over tissue containing water so as to safely achieve the desired effects on lipid-rich tissue in performing a therapeutic procedure.

SUMMARY OF THE INVENTION

In accordance with the above, this invention provides a method and apparatus for selectively targeting lipid-rich tissue to effect a desired treatment, the method/apparatus involving irradiating the lipid-rich tissue at an infrared wavelength at which the ratio of absorption of the radiation by lipid-rich tissue to absorption by water is 0.5 or greater, and preferably greater than one. In particular the irradiation is preferably at a wavelength between 880–935 nm, 1150 to 1230 nm, 1690 to 1780 nm, or 2250 to 2450 nm with a fluence and for a duration sufficient to treat such lipid-rich tissue. For preferred embodiments, depending on application, the irradiation wavelength is between approximately, 900 to 930 nm, 1190 to 1220 nm, 1700 to 1730 nm, or 2280 to 2360 nm, with approximately 920 nm, 1210 nm, 1715 nm, and 2300 nm being most preferred wavelengths. While the fluence and duration of irradiation will vary somewhat with the patient undergoing treatment, the anatomical location of the tissues being treated, the radiation source and wavelength, the size of the lipid-rich tissue being treated and other factors, for preferred embodiments the treatment fluence may for example be approximately 0.5 J/cm$^2$ to 500 J/cm$^2$, with the duration of treatment pulses being approximately 10 $\mu$s to several seconds, or even minutes for photothermal effect, and less than 1 $\mu$s (i.e., generally 1 $\mu$s to 1 ns) for photomechanical effects.

Where the lipid-rich tissue being treated is one or more sebaceous glands, irradiating the tissue/gland is performed by applying the energy at an indicated wavelength, which wavelength is preferably in one of the higher bands, to the skin surface overlying such one or more sebaceous glands. Where the lipid-rich tissue is subcutaneous fat, energy may be applied to the skin surface overlying the subcutaneous fat to be treated. Where either the sebaceous gland or subcutaneous fat is treated through the overlying skin, and particularly for subcutaneous fat, the radiation is preferably applied through an applicator which applies pressure to the skin above the lipid-rich tissue being treated. This pressure reduces the distance from the radiation-applying applicator to the lipid-rich tissue being targeted, removes blood from the area above the fat tissue being targeted and compresses such overlying tissue to reduce scattering and enhance optical focusing of radiation on the treatment area. It is also desirable that the skin above the area being treated be cooled to a selected depth, which depth is above that of the lipid-rich/fat tissue being targeted. Thus, cooling could be deeper for the treatment of subcutaneous fat, where the cooling could be most of the way through the dermis, while the cooling would be to a much shallower depth, perhaps only to the dermis/epidermis (DE) junction, where the sebaceous gland is being treated. While radiation in the higher bands can be used, and may be preferable because of the higher absorption coefficient of fat in these bands, for treating the sebaceous gland which is relatively close to the skin surface, absorption by water at these wavelengths make it difficult to reach subcutaneous fat, and radiation in the lower bands, for example in 1150 to 1230 nm range where water is less absorbent may therefore be preferable for treating subcutaneous fat. In addition to or instead of pressure being applied to the skin, a fold of skin may be drawn into a recess in a radiation delivery head in a suitable manner and radiation applied to the recess from at least two directions. This has a number of beneficial effects, including reducing the distance from the radiation source to the lipid tissue, increasing the radiation at the desired depth without increasing radiation in regions above the target area and, where a retroreflection technique to be discussed later is utilized, substantially eliminating radiation loss as a result of the scattered radiation reflected from the patient's skin. Alternatively, to increase the local intensity for treatment of subcutaneous fat when delivered through the overlying skin, a convergent incident beam is advantageous to compensate for losses due to optical scattering and absorption in the dermis.

While the sebaceous gland may be heated to destroy the gland as part of an acne treatment, the sebaceous gland may also be heated to cause destruction of adjacent areas of a hair follicle, for example the stem cells of the hair follicle as a treatment to achieve hair removal and impede regrowth. Radiation in the indicated wavelengths may also be applied selectively to cells having lipid-rich membranes to porate the membranes to for example permit selective drug delivery to the cells or for other purposes for lipid-rich cells or tissue may be otherwise targeted and heated for affecting some other therapeutic function. Since the radiation fluence, pulse duration, wavelength and other factors may be carefully controlled, and the area to which the radiation is directed may also be controlled, selective lipid-rich cells may be non-invasively targeted to achieve the above and other therapeutic affects.

Where subcutaneous fat is being non-invasively treated, duration of radiation pulse and the temperature to which the fat or lipid tissue is heated are critical to the desired results.

For example, at increased temperature, fat is altered by a biochemical reaction or lipolysis, while for higher temperatures and sufficient pulse duration, fat cells are killed, permitting the cells and liquid lipid therein to be absorbed. At still higher temperatures, cell membranes are destroyed, permitting lipid pools to be formed. These pools may also be absorbed but, since free fatty acid in lipid can be toxic in sufficient quantity, if substantial quantities of fat cell membranes have been destroyed, permitting a large lipid pool to be formed, it is preferable to remove the lipid, for example with a cannula or needle. The heated collagen of supporting structure may react to provide a more pleasing skin appearance after treatment and avoid sagging folds of skin or skin depressions where the lipid tissue has been destroyed. While all of the fat in a subcutaneous layer may be treated, it is difficult to get sufficient energy deep into the fat, so treatment is generally restricted to a surface layer of the fat. Repetitive treatments may be performed to remove successive layers of the subcutaneous fat.

While non-invasive procedures are preferable, subcutaneous fat may also be treated by passing a probe through the skin to the subcutaneous fat to be treated. The probe, which may for example be a needle, may be passed into the subcutaneous fat at an angle to the skin surface and the probe may be moved both in an out of the skin and rotated about its skin entry point to irradiate and treat subcutaneous fat over a selected area. This needle or probe may also contain a cannula for removing liquid lipid pooled as indicated above from the radiation treatment Where lipid-rich tissue/fat surrounds a vessel, organ or other anatomical element on which a surgical or other procedure is to be performed, the irradiation may be performed by use of a tool which is in at least near contact, and preferably in contact, with the fat to be treated, the element treating the fat to expose the anatomical element on which the procedure is to be performed. Because radiation for this embodiment does not need to pass through water rich tissue to reach the fat, wavelengths in the higher bands would normally be used for this procedure.

While various light sources might be utilized to obtain optical energy within the required bands, and in particular at the preferred wavelengths, including a suitably filtered tungsten lamp, an optical parametric oscillator, a Raman convertor or shifter, a color center laser or a tunable dye laser, the preferred light source at the desired wavelengths is a diode laser or lasers with flashlamp or diode pumping which will be described in greater detail later.

The foregoing and other objects, feature and advantages of the invention will be apparent from the following more particular description of preferred embodiments of the invention as illustrated in the accompanying drawings:

IN THE DRAWINGS

DETAILED DESCRIPTION

Figure 1:
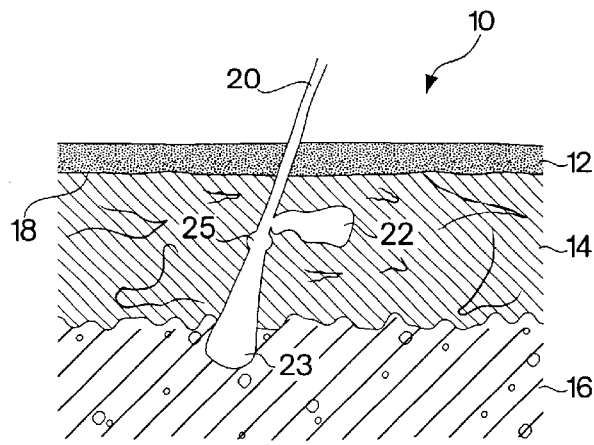
FIG. 1 is a diagrammatic sectional view of human skin illustrating both a hair follicle with a sebaceous gland and subcutaneous fat.

FIG. 1 is a simplified sectional view through a piece of human skin 10 illustrating the major skin layers. The outermost layer is the epidermis 12 which overlies the dermis 14. Under the dermis is a layer of subcutaneous fat 16. The epidermis is typically relatively thin, on the order of 0.1 mm, although this thickness varies for different parts of the body, with the lower portions of the epidermis near the DE junction 18 containing quantities of melanin which vary with the pigmentation of the individuals skin. The thickness of dermis layer 14 varies from approximately 1 to 5 mm depending on the part of the body and on the individual, and may be thicker in some instances. The lower third of the dermis typically contains numerous lobules of fat. Subcutaneous fat 16, which may be several centimeters thick, therefore generally starts at a depth of a little less than 1 mm to approximately 4 mm from the skin surface.

FIG. 1 also illustrates a single hair follicle 20 with an adjacent sebaceous gland 22. Hair follicle 20 has a bulb or papilla 23 and stem cells in a bulge region 25, both of which are involved in the growth and regrowth of hair from the follicle. Sebaceous glands 22 are formed primarily of fat/lipid-rich tissue. The cells lining the outer portion of sebaceous glands are called sebocytes. These cells migrate inward, synthesizing a lipid-rich fluid called sebum as they differentiate and finally are shed. The sebum flows outward through a duct into the infundibulum ("pore") of the follicle. The greasy, oily material which accumulates on the surface of skin is sebum, after flowing out of numerous follicles. When the outflow from a sebaceous gland becomes clogged, it may result in the formation of an acne pimple. This is a particular problem for larger sebaceous glands, for example those on the face and upper back, which are the most common sites of acne. Sebaceous glands are typically found approximately 1 mm below the skin surface, although they may be at greater depths in some instances, and are in the dermal layer 14 as shown in FIG. 1.

While as was discussed earlier, various techniques have been used in the past to remove unwanted fat, and there has been limited use of lasers for treating fat tissue, since there was not selective absorption by lipid-rich tissue for the wavelengths at which such procedures were conducted, such fat treatment could generally be done only through a surgical procedure which permitted the laser to be brought directly adjacent or in contact with the fat tissue to be treated. However, because of the low absorptions of fat at such wavelengths, and the high ratio of water absorption to fat absorption, very high energy was required for treatment and extreme care had to be exercised so as to avoid unintended damage to other tissue either adjacent to or underlying the fat tissue to be treated. As a result, such procedures have not been used to any significant extent.

In order to determine a preferential wavelength for lipid absorption, it should be appreciated that the temperature rise in a given tissue as a result of absorbing a given amount of energy is a function of the density of the tissue and its heat capacity. When this temperature increase for absorbed energy is compared for water and fat or lipid-rich tissue, it is found that the temperature rise in the lipid-rich tissue for a given energy absorption is 1.8 to 2 times that for water. Therefore, lipid-rich tissue need absorb 0.5 to 0.6 as much energy to achieve the same temperature rise as for water. Thus, for purposes of the following discussion, it will be assumed that lipid tissue preferentially absorbs at a wavelength for which the coefficient of absorption for fat is at least 0.5 that of water, although this ratio for preferred wavelengths is at least 1 and is 1.5 or higher for selected wavelengths.

Figure 5:
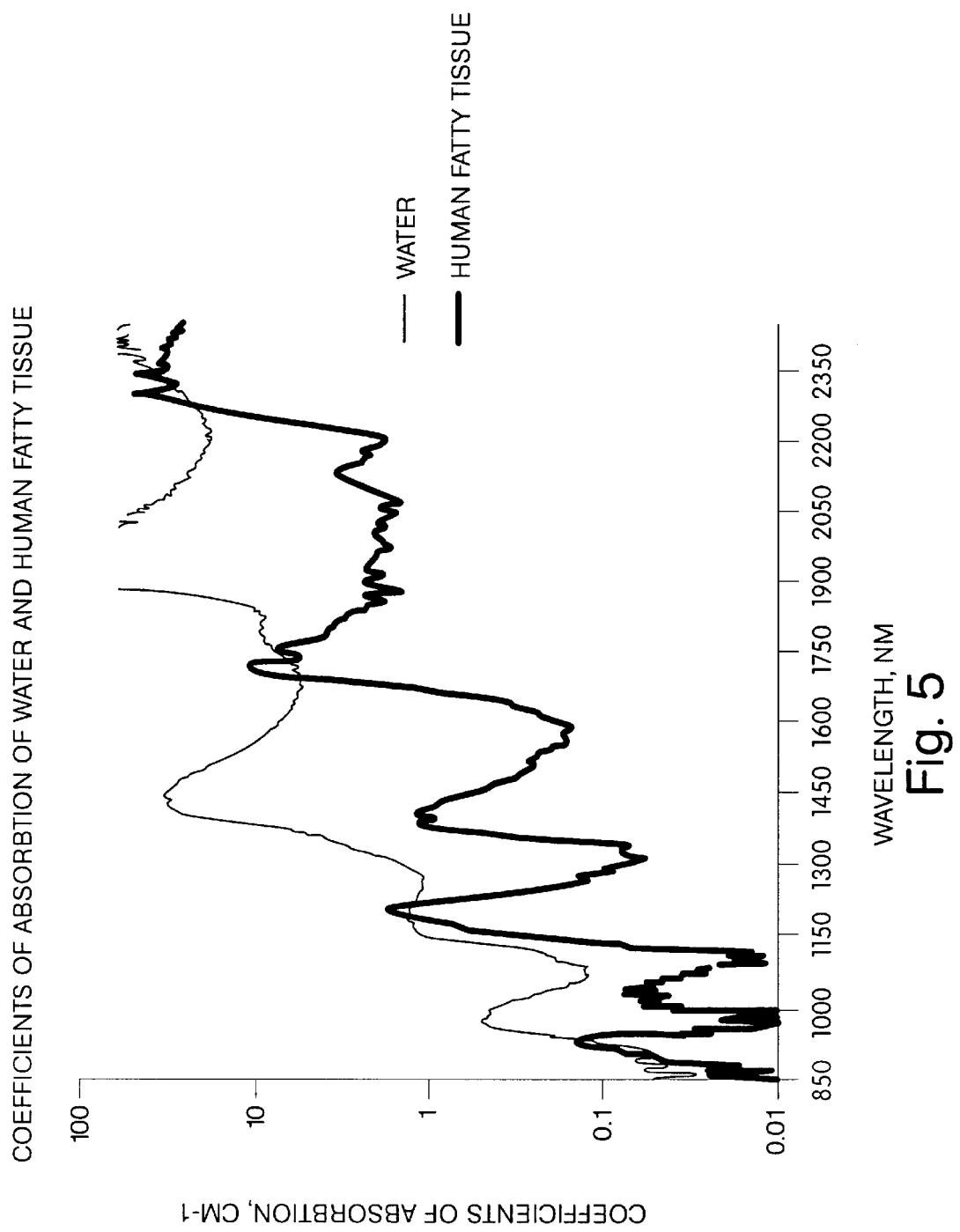
FIG. 5 is a graph illustrating the coefficient of absorption of water and of human fatty tissue as a function of wavelength.
Figure 6:
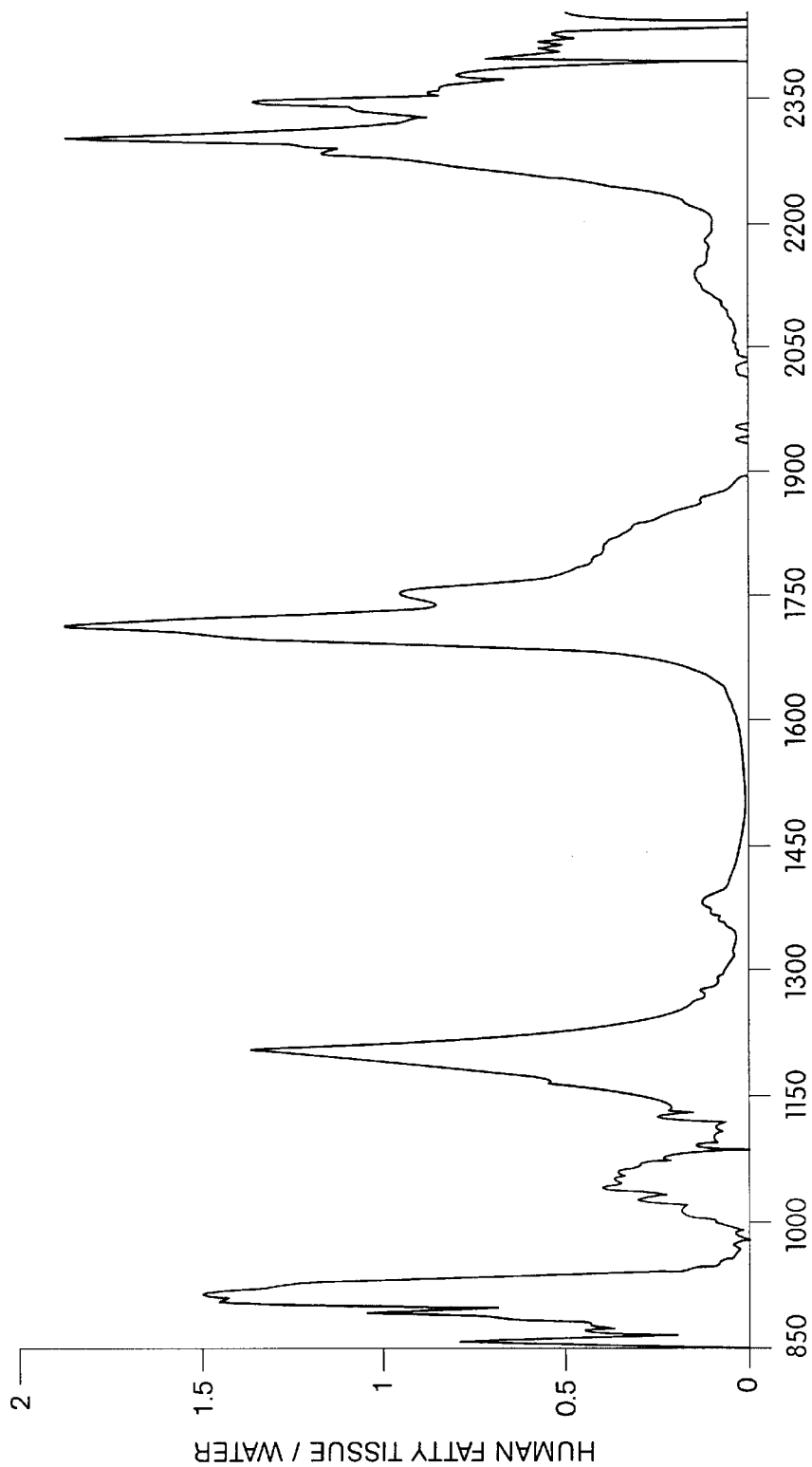
FIG. 6 is a graph illustrating the ratio of human fatty tissue coefficient of absorption to water coefficient of absorption as a function of wavelength.

Thus, as illustrated in FIGS. 5 and 6, and in accordance with the teachings of this invention, it has been discovered that for wavelengths between approximately 880 nm and 935 nm, 1150 and 1230 nm, 1690 and 1780 nm, or 2250 and 2450 nm, lipid has at least 0.5 the absorption of water, and generally greater absorption than water, water being the major constituent of lipid-poor tissue. This absorption is attributed to a vibrational mode in the C=H and C—H bands common in lipids. These wavelength bands also are readily compatible with silica optics. For these regions, the absolute absorption by both water and lipid increases with increases in the wavelength (i.e., both water and lipid absorb most strongly in the 2250 to 2450 nm range and absorb least strongly in the 900 to 930 nm range). The ratio of lipid absorption to water absorption is also greater for the higher wavelengths, being over 1.5 for maximas at approximately 1715 nm and 2300 nm. Therefore, radiation within the above-indicated wavelength bands, and in particular radiation at or near various maxima in these bands such as 925 nm, 1210 to 1230 nm, 1715 nm, or 2300 nm would be particularly effective for treating lipid-rich tissue such as sebaceous glands or subcutaneous fat. However, the depth which light/radiation reaches in a patient's skin is inversely proportional to light absorption above such depth. Since water is the primary constituent of skin tissue, water absorption is a controlling factor in the depth which radiation of a particular wavelength may reach in a patient's skin. Therefore, radiation in the 900 to 930 nm band and 1210 to 1230 nm band which are most weakly absorbed by water, while still being at least somewhat strongly absorbed by fat, are the currently preferred radiation bands for non-invasively treating subcutaneous fat, where the radiation generally needs to reach at least 3 to 4 mm within the patient's skin. However, radiation in the higher bands, and particularly at 1200 nm (with focusing), 1715 nm, and 2300 nm wavelengths, may be preferable for treating the sebaceous gland which is generally located only 1 mm into the patient's skin, since fat absorbs more strongly at these wavelengths and water absorption in the overlying skin is not as big a factor. The longer wavelengths could also be used where a suitable light emitting probe is positioned adjacent the fat to be ablated, for example to clear fat from a vessel, organ or the like or where a needle is used to get to subcutaneous fat.

The first issue in implementing the teachings of this invention is to find a radiation source adapted for generating sufficient radiation at the required wavelengths. Unfortunately, while commercially available lasers or other radiation sources are available for the 900–930 nm range and YAG lasers operate at approximately 1060 and 1300 nm, current commercially available lasers/radiation sources are not normally adapted for generating radiation at the other preferred wavelengths. However, there are lasers and other radiation sources suitable for generating such radiation.

For example, the following light sources with wavelengths around 920, 1200, 1715, or 2300 nm can be used for fatty tissue targeting:

1. Tungsten lamp or an arc lamp with an absorptive or reflective filter which filters the required spectral region. Optimum lamp temperature is in the region 1300–2000 K.

2. Tungsten lamp or an arc lamp with a luminescence filter with a peak of luminescence at one of the spectral regions described above. As a filter, the following can be used: crystals with color centers, liquid dyes or dyes in a solid matrix.

3. Diode lasers, such as GaAs (920 nm), AlGaSbAs (1200, 1215 nm), InGaAsP/InP (1715 nm), InGaAs (2300 nm).

4. Lasers based on crystals with color centers and lamp or laser pumping. These would include crystals NaF with $F^{2+}$ centers (1200 nm) or KCl with $F^{2+}$ centers (1215 nm) or KClLi with $F^{2+}$ centers (2300 nm).

5. Lasers with non-linear wavelength conversion; optical parametric oscillators (OPO) or Raman converters can be used as such non-linear converters. Solid state lasers can be used for pumping (Nd laser, Ho laser, Er laser, fiber laser etc.) of OPO or Raman converter.

6. One of the most effective lasers can be a lamp pumped solid state laser with correct spectral lines. For example crystals with ions $Er^{3+}$ can generate in the region 1200 nm ($^4S_{3/2} \to {}^4I_{11/12}$) and 1715 ($^4S_{3/2} \to {}^4I_{9/2}$).

For operating in the 1700 to 1730 nm range, one suitable laser is a potassium cadmium laser with the matrix KCd $(WO_4)_2$ which is doped with $Er^{3+}$ (erbium) ions. The concentration of $Er^{3+}$ ions should be in the range of 1–10 percent, with the optimal concentration being approximately 2–5 percent. The energy level transition $^4S_{3/2} \to {}^4I_{9/2}$ should be used for laser generation. For both levels $^4S_{3/2}$ and $^4I_{9/2}$, Stark broadening and the wavelength for maximum laser output depend on the relative orientation of the crystal axis, laser radiation axis and polarization of laser radiation. When the orientation is such that the axis of the laser beam is at an angle greater than 45 degrees with the crystal line axis [010], the spectral maximum of the laser output is at the desired 1715 nm wavelength. Maximum efficiency is achieved when the axis of the laser beam lies in the plane determined by the crystalline axis [100] and [001 ] and is directed along the optical axis $N_m$ which forms an angle of 24 degrees with crystalline axis [100]. If the same crystal is used for laser generation along the crystalline axis [010], the wavelength of laser generation for the same transition is 1730 nm. Flashlamps, laser diodes, other lasers or other pump mechanisms can be used to pump the above crystal in order to achieve the desired wavelength output.

In order to obtain maximum efficiency, the following scheme might be used to provide the desired radiation:

A diode laser generating an output at approximately 920 nm is used to pump a Yb doped glass or fiber with a laser wavelength of 1100 nm. This output is then frequency-doubled to obtain a wavelength of 550 nm which is the most efficient pumping wavelength and may be utilized for direct pumping of the $^4S_{3/2}$ level. The maximum efficiency would be 0.6 (diode)×0.3 (fiber laser)×0.7 (doubling)×0.3 (Er laser)=3.75 percent. With this laser, it is possible to achieve generation of wavelengths 850 nm ($^4S_{3/2} \to {}^4I_{13/2}$ transition) and 1220 nm ($^4S_{3/2} \to {}^4I_{11/12}$ transition), along with the generation at wavelengths 1715 nm or 1732 nm. The laser can work simultaneously at various combinations of these wavelengths including:

$\lambda$=1715 nm and $\lambda$=850 nm, or $\lambda$=1715 nm ($\lambda$=1730 nm) and $\lambda$=1210 nm, or
$\lambda$=1715 nm ($\lambda$=1730 nm), $\lambda$=1210 nm and $\lambda$=850 nm.

Laser light from pumping diode laser (920 nm) can also be used for selectively heating fat. Control over the spectral distribution is achieved by changing mirrors or by a dispersive element inside the laser cavity.

Radiation at 1730 nm, may be obtained if lasers based on YLF, YAG, YAL, YSGG or a fiber doped with $Er^{3+}$ ions are used. In these lasers, the same transition where $^4S_{3/2} \rightarrow {}^4I_{9/2}$ is used, and the ion concentrations and the pumping methods would be substantially the same as for the preferred laser indicated above, but as indicated previously, would result in an output at 1730 nm, which is not one of the most optimal wavelengths for lipid-rich tissue ablation, although still suitable for this purpose. Its combination with $\lambda$=1210 nm and $\lambda$=850 nm is also possible. Pumping methods and concentration of active ions is the same as for the KCd $(WO_4)_2:Er^{3+}$. The concentration of $Er^{3+}$ ions should be in the range 1–50%, with an optimal ion concentration being in the range 2–5%.

Radiation at 1730 nm may be achieved using for example, an $YLF:ER^{3+}$ with concentration of $Er^{3+}$ 25% laser with flashlamp pumping. For this laser, the maximum output energy is 1 J, slope efficiency is 0.5%, repetition rate is 4 Hz and the pulse width is 0.4 ms.

Certain diode lasers may also be utilized to generate radiation within the desired wavelength ranges. For example, a laser based on InGaAsP/InP can generate laser output in a range of wavelengths about 1700 nm with fine temperature tunability and stabilization. Blackbody sources, such as a tungsten lamp with suitable optical filters, can also be used to produce the desired radiation. However, the spectral power and tissue selectivity of such light sources would be less than for laser sources. The optimal temperature of the heat source should be about 1700 degrees K, with approximately 5 percent of the radiation of the lamp operating at this temperature being in the spectral region between 1700 nm and 1760 nm. Further, while the desired wavelengths can also be achieved by a tunable laser like a dye laser, free electron laser, color center laser or Raman shifter, the efficiencies of these lasers is low and they are very expensive. They are therefore not as practical as other sources for this application. Finally, an optical parametric oscillator (OPO) with pumping from a solid state laser or a fiber laser could also generate energy at the desired wavelengths. An OPO has maximum efficiency only for very short pulses, and would be most useful therefore when treatment is accomplished by photomechanical or photodissociation at 1 ns to 4 fs interactions. Other light sources generating radiation within the indicated wavelength band might also be utilized in appropriate applications.

The time of exposure at a given site can be effectively used over a very wide range, but is preferably within either of two regions causing photothermal or photomechanical effects. For photothermal damage, or necrosis of lipid-rich tissues including fat and sebaceous glands, exposure durations of 0.1 ms to several minutes and sometimes higher are desirable, depending on the size of the targeted structure (for example the sebaceous gland diameter or subcutaneous fate depth being treated). For photomechanically-mediated damage, or necrosis, e.g. by violent castation, shock waves, or spallation, an exposure of less than 1 microsecond is desirable, and less than 10 $\mu$s is most preferred. The longer exposure duration can be generated for example by a flashlamp-pumped laser, scanned or shuttered CW laser, or conventional sources described above. The shorter exposure durations, less than 10 $\mu$s can be generated by Q-switching or mode-locking of laser cavities, or by an OPO or Raman-shifted Q-switched laser as described above.

Figure 2A:
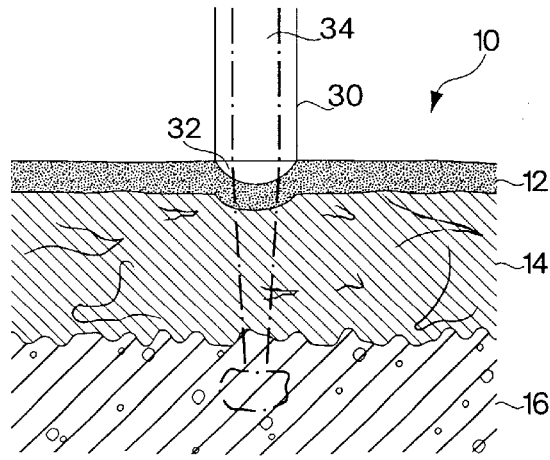
FIG. 2A is a sectional view illustrating an area of subcutaneous fat under treatment in accordance with the teachings of a first embodiment of this invention.

FIG. 2 illustrates one way in which the teachings of this invention might be utilized to non-invasively treat either subcutaneous fat 16 (as shown in the figure), at least one sebaceous gland 22 or other targeted lipid-rich tissue. For this embodiment of the invention, an applicator 30, which could for example be of the type shown in U.S. Pat. Nos. 5,595,568 or 5,735,844, is utilized. Applicator 30 may have a lens 32 or other suitable contact element at the front end thereof, which element is adapted to be in pressure contact with the upper surface of epidermis 12, thereby deforming the skin in the contact area for example as shown in FIG. 2. Applying pressure to the skin in this way provides a number of advantages. First, the pressure reduces the distance between the laser source and the sebaceous gland 22/subcutaneous fat 16, thereby reducing the amount of tissue through which the light must pass prior to reaching the area under treatment. While radiation within the indicated bands is preferentially absorbed by the lipid-rich tissue, there is still absorption by the water/blood-containing tissue above the lipid-rich tissue being treated. Therefore, the greater the reduction in the quantity and thickness of this tissue, by for example tension, the less energy is lost in this tissue, resulting both in more energy being available for treatment at the desired location and in less heating, and therefore less potential thermal damage, to the lipid-poor tissue not under treatment.

The second advantage is that if the pressure is above the body's blood pressure (e.g., about 3 psi), the pressure will force blood out from under the applicator, further reducing absorption in the lipid-poor tissue through which the radiation passes. It has also been found that compressed tissue causes significantly less scattering of light energy passing therethrough, or in other words is more transparent to such light energy, when under significant pressure than when not under such pressure. Not only does this phenomenon reduce radiant energy loss, and thus heating in the tissue above the tissue under treatment, but it also permits more effective focusing of light energy to facilitate heating and/or damage of only desired tissue. Thus, light could be focused to a depth of approximately 1 mm for treatment of lipid-rich sebaceous glands to for example treat an acne problem or for hair removal, and could be focused to a depth of for example 3 or 5 mm for treatment of subcutaneous fat 16. FIG. 2 shows an exemplary such focused radiation beam 34 being directed to the upper portions of subcutaneous fat layer 16.

However, while applying pressure has some advantages, it is also disadvantageous in that blood flowing through the dermis is one effective way of removing heat so as to protect this area. This disadvantage needs to be balanced against the previously discussed advantages in deciding on whether to utilize pressure.

One problem with applying energy to the sebaceous gland 22 or to subcutaneous fat 16 through the overlying epidermis and dermal tissue is that, even though the overlying tissue do not preferentially absorb radiation at the indicated wavelengths, they do as can be seen from FIG. 5, and depending on wavelength, absorb significant radiation and can therefore become heated. Such heating can cause potential temporary skin damage or permanent scarring, with permanent scarring occurring primarily in the dermis 14. Blistering, peeling, and depigmentation are other potential adverse affects which may result from the heating of tissue above the lipid-rich tissue under treatment.

Therefore, it is preferable that the epidermis and dermis above the lipid-rich tissue being treated be cooled at least prior to and preferably both prior to and during, the application of the radiation to minimize thermal damage to tissue in these areas. However, it is also important that the cooling not extend to the lipid-rich tissue being treated since such cooling would impede the treatment of this lipid-rich tissue and may prevent the desired treatment thereof. Therefore, when the sebaceous gland is being treated, cooling should not extent below or much below the DE boundary layer 18, and certainly should not extend much beyond 1 mm from the skin surface. Where subcutaneous fat 16 is being treated, the cooling may extent several millimeters into the dermis, depending on the thickness thereof. The cooling may be performed in the manner indicated in the before-mentioned patents or by other techniques known in the art. In particular, cryogenic cooling may be utilized to cool the skin to a predetermined depth prior to irradiation, or contact piece 32 may be cooled by flowing water or gas, or preferably by semiconductor Peltier effect cooling as taught in co-pending application Ser. No. 08/759,136. The temperature of for example contact piece 32 and the time during which this piece is in contact with the skin prior to irradiation will be primary factors in determining the depth of cooling.

The energy or fluence required to heat to a desired temperature and/or destroy targeted fat and the duration of the light pulses used for this purpose will vary, sometimes significantly, with the individual being treated, the area of the body being treated, the specific lipid-rich/fat tissue which is to be treated and the wavelength utilized. For a sebaceous gland 22 having a diameter which is generally in the 0.5 to 3 mm range, which is typical for sebaceous glands being treated which are frequently larger sebaceous glands, a fluence of approximately 10 J/cm$^2$ to 500 J/cm$^2$ applied for a duration of approximately 10 ms to one second depending on the size of the gland, should result in destructive heating or other treatment of sebaceous glands in most instances, particularly if the pressure and cooling procedures discussed in the preceding paragraphs are followed. Higher fluencies are required if shorter wavelengths are used (for example 920 nm or 1200 nm) because of the lower absorption coefficient of fat at these wavelengths.

While because of the higher absorption of lipid tissue at the longer wavelengths, wavelengths such as 1715 nm, or 2300 nm may be utilized for targeting of a sebaceous gland 22 or for treatment when the light source is adjacent the lipid-rich tissue, for non-invasive treatment of subcutaneous fat, particularly in region where the dermis is 3 to 4 nm thick, the high absorption of water at these wavelengths effectively prevents radiation at these wavelengths from penetrating to reach the subcutaneous fat layer, even when relatively high fluence signals are utilized. However, at the shorter wavelengths, for example 920 nm or 1200 nm, water is significantly less absorbent, permitting a significant percentage of the applied radiation to reach at least the upper level of subcutaneous fat layer 16. However as may be seen from FIG. 5, fat also has a significantly lower coefficient of absorption at these wavelengths than at the higher preferred wavelengths, meaning that more energy must be applied to the fat in order to achieve the same level of heating. For example, almost 10 times the energy must be applied to the fat at 920 nm as at 1200 nm in order to achieve the same heating of the fat, and the heating increases by nearly another six times for the same energy at 1715 nm. At 2300 nm, the energy absorbed is about five times greater than at 1715. However, beyond 1300 nm, substantially all energy applied to water-rich tissue is absorbed in passing through several millimeters of skin, and it is therefore very difficult, even with pressure, for radiation at these wavelengths to be used for non-invasively targeting subcutaneous fat, except possibly in areas such as sacks under the eyes or in the neck where this fat may be closer to the surface. Therefore, it is currently contemplated that radiation in the band around 1200 nm is the best compromise between energy reaching the subcutaneous fat through the overlying tissue and the radiation being of a wavelength which is absorbed sufficiently by the fat tissue to cause a desired treatment to occur.

The mechanism by which the fat is destroyed or otherwise reduced will vary to some extent with the duration of radiation pulses and the temperature to which the fat is raised. If the fat cell temperature is raised slightly from body temperature of about 37° C. by for example less than 10° C., no lethal injury occurs to most of the cells. This temperature rise does however initiate a biochemical reaction or lipolysis in the fat cells causing the cells to metabolize fat, or accelerate the metabolization thereof, thereby reducing the level of fat. At higher temperatures, for a sufficient duration, depending on size, fat cells are killed. As with most dead cells, the body ultimately absorbs and disposes of these cells. At still higher temperatures, for example above 60° C., the walls or membranes of the lipid cells, which walls are primarily of lipid-rich material, are blebed, losing their ability to encapsulate the liquid lipid therein, the liquid lipid leaking therefrom to form pools which will also ultimately be absorbed by the body. However, liquid lipid contains free fatty acid which, in sufficient quantity, can be toxic to the human body. Therefore, if a substantial pool of liquid lipid is formed in this way, it is preferable that a hypodermic needle be inserted into this pool and that at least most of the liquid lipid be removed through the hypodermic needle so as to limit the amount thereof which is absorbed into the body. Typically, both because of the limited depth to which significant radiation can be applied in the subcutaneous fat layer and for other reasons, the blebed cells would generally only extend for a few millimeters into the subcutaneous fat layer, for example 2 to 3 mm. Pooled liquid lipid may also be removed by perforating the skin above it and permitting it to drain or by facilitating drainage by manipulation/massage of the area or other techniques known in the art.

The advantage of the above procedure is that, so long as the temperature is kept low enough, for example below approximately 70° C. or other collagen damage threshold, there will be no damage to the collagen bands which hold the skin to the body, and in fact these bands may be contracted by the heat. This maintains skin tone, notwithstanding the removal of the underlying subcutaneous fat and reduces sagging skin or dimples in the treated skin area. While if the temperature of fat cells was raised high enough, the lipid could be melted, eliminating the need for the body to either absorb it or for it to otherwise be removed, and such procedure is also within the contemplation of the invention, it is not currently believed to be a preferred procedure because of the damage to the collagen bands in the subcutaneous fat layer and other problems which might occur at these elevated temperatures.

A possible procedure when using the teachings of this invention for ablating subcutaneous fat would be to place a cooling hand piece 32 in contact with the patient's skin, probably under at least some pressure, for a time sufficient to cool the skin to a desired level, perhaps 5 to 10 seconds. Because of hot blood flowing through the dermis, cooling generally levels off after roughly this duration and cooling to greater depth is not achieved.

Once the precooling has been completed, the radiation source, for example the laser, is activated for an appropriate period of time, perhaps 1 to 100 seconds. The required fluence and pulse duration can be calculated or can be determined empirically by using microwave or ultrasonic depth measuring techniques or other techniques known in the art for measuring temperature at depth. Another option is to insert a needle into the area where a liquid lipid pool should be formed if the heat was sufficient to bleb the cell membranes to see if a liquid pool has been formed. If a liquid pool has not been formed, then treatment is required at either a higher fluence or for longer duration. This procedure can be repeated until liquid lipid is obtained. The area from which the liquid lipid is being removed may be manually manipulated or "milked" to facilitate the removal of the liquid lipid pool.

Figure 2B:
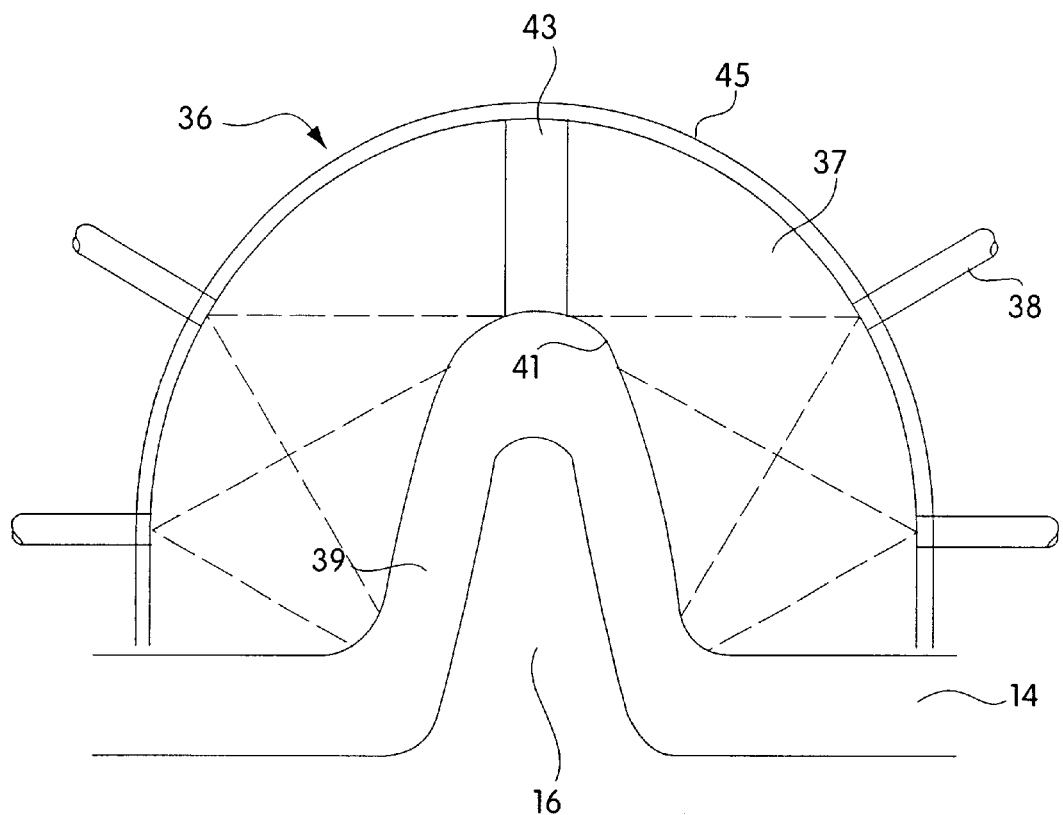
FIG. 2B is a sectional view illustrating an area of skin, either subcutaneous fat, sebaceous gland or other targeted lipid-rich tissue, under treatment in accordance with an alternative embodiment of the invention.

Since substantial fluence may be required in order to ablate subcutaneous fat in the manner indicated above because of both the energy loss in the overlying layers and the relatively low coefficient of absorption for the fat at the wavelengths which must be used to reach the subcutaneous fat, the head used for applying radiation should preferably utilize a photorecycling technique, such as that taught in U.S. Pat. No. 5,824,023 or in application Ser. No. 09/268, 433 filed Mar. 12, 1999, now U.S. Pat. No. 6,508,813 entitled "SYSTEM FOR ELECTROMAGNETIC RADIATION DERMATOLOGY AND HEAD FOR THE USE THEREWITH." In conjunction with photorecycling, another way of more efficiently getting energy to an area under treatment is to pinch a fold of skin containing the treatment area in a section of the radiation emitting head, facilitating the application of radiation to the treatment area from at least two directions. Such techniques are taught, for example in U.S. Pat. No. 5,735,844 and in application Ser. No. 09/473,910 filed Dec. 28, 1999, now U.S. Pat. No. 6,517,532 entitled LIGHT ENERGY DELIVERY HEAD, the contents of which are incorporated herein by reference. FIG. 2B illustrates an embodiment 36 of the invention which practices this pinched-fold technique. For this embodiment, the head is formed of an optically transparent dielectric material 37 such as sapphire or glass and has a plurality of optical fibers 38 affixed thereto or embedded therein which fibers are angled to impinge on a fold of skin 39 drawn into a recess 41 formed in material 37. Recess 41 might for example ½ inch across. The head and recess may be relatively shallow with only the fibers 38 shown in the figure or the head and recess may extend for a selected width into FIG. 2B and additional fibers 38 may be provided at selected points along such width. A hole or groove 43 is provided to which negative pressure or vacuum may be applied to draw the fold of skin into groove 41 and a high reflecting coating 45 may be applied to the outer surface of material 37. Coating 45 is effective to retroreflect radiation exiting skin fold 39 back into the skin in a manner discussed in the prior patent/application to enhance energy efficiency, thus permitting more radiation to reach a desired site for the same energy from a radiation source. Optical fibers 38 can be angled to target a desired lipid-rich tissue region in fold 39.

While in the discussion above, required fluence has been more or less empirically determined, in some applications, the required fluence can be estimated by use of the following equation:

$$P = \frac{\rho_f \cdot c_f \Delta T \cdot d}{\left(1 - e^{\frac{\tau}{\tau_1}}\right) \cdot \tau_1 \cdot \left(1 - e^{-\alpha_f d}\right)} \quad (1)$$

Where P is power density, ΔT is temperature rise required from normal body temperature of approximately 37° C. to achieve lipid heating in accordance with the selected technique discussed above, d is the size of the targeted lipid region, for example the diameter of a sebaceous gland or the depth in for example subcutaneous fat or fat surrounding an organ, vessel or the like which is to be targeted, $\tau_1$ is a thermal relaxation time of the fatty tissue targeted, τ is pulse width, $\alpha_i$ is absorption coefficient of the fatty tissue, $\rho_f$ is the density of the fat and $c_f$ is the heat capacity of the fat. Fluence (E) is given by:

$$E = P\tau \quad (2)$$

Thermal relaxation time for fatty tissue can vary from several nanoseconds for lipid in the membrane of a cell, to seconds (for example for a sebaceous gland), to several hours (for example for subcutaneous fat).

Using the above equations, and assuming a temperature rise ΔT in the fat of approximately 13° C., to 50° C., the fluence required to be applied to the skin for a wavelength of 920 nm is 50–500 J/cm², the fluence required to be applied to the skin at 1200 nm is roughly 10–100 J/cm² and the fluence for 1715 nm is 1–50 J/cm². The low value in these ranges assumes the fat to be treated at substantially the skin surface with the fluence increasing as the depth of the fat being treated increases, the highest value being for subcutaneous fat at a depth of approximately 4 mm. Since at the other preferred wavelength band, radiation applied to the skin will not normally reach subcutaneous fat, for this wavelength band it has been assumed that the radiation is applied directly or nearly directly to the fat cells, differences in range being accounted for by differences in size or depth of the lipid cells being treated, pulse width and the temperature to which the fat is to be raised. With these assumptions, at 2300 nm, the fluence range is 0.5–20 J/cm².

Where the pulse duration is longer than the thermal relaxation time of the fat cells or tissues being heated, this being sometimes referred to as quasi-stationary heating, power densities required for selective damage of or initiation of biochemical processes in the fatty tissue are estimated to be in the following range:

920 nm: 500–2000 W/cm²
1200 nm: 50–500 W/cm²
1715 nm: 10–200 W/cm²
2300 nm: 5–50 W/cm²

The first three of these values are taken at the skin surface, while the last one is taken at the surface of the lipid tissue.

While in the discussion above, the sebaceous gland 22 has been targeted for destruction as a treatment for acne, the sebaceous gland, being located close to the stem cells 25 of a hair follicle 20, may be targeted for other therapeutic purposes. In particular, the fat in the sebaceous gland could serve as a chromophore which is preferably heated by radiation at one of the selected wavelengths, the heat from the sebaceous gland if at a relatively low level being sufficient to sever the hair shaft at the level of the sebaceous gland, which hairs may then be washed away. This would be the equivalent of a shave which might last several weeks. More intense targeting of the sebaceous gland could result in sufficient heating to destroy the stem cells of the follicle which could sufficiently damage or destroy the follicle to provide long term or even permanent hair removal. This technique would be particularly advantageous for people having very light hair and light skin with little melanin in either the hair shaft or follicle, melanin being the chromophore normally used in other radiation hair removal techniques.

Another mechanism by which the teachings of this invention could be used for hair removal stems from the fact that papilla or bulb 23 is located in the upper regions of subcutaneous fat 16. Therefore, heating subcutaneous fat in the region of a hair follicle in the manner previously discussed will also result in a heating of the bulb/papilla of the hair follicle which can damage or destroy these structures. Damage or destruction of the bulb or papilla is another mechanism by which hair removal is effected.

The teachings of this invention may also be utilized to target lipid-rich tissue in other regions for other purposes. For example, the stratum corneum contains a layer of lipid tissue which serves as liquid barrier in a persons epidermis. This liquid barrier can reduce the effectiveness of needless injections which rely primarily on pressure to inject a liquid agent into the patient. A short burst of radiation at one of the wavelengths indicated above, for example 1715 nm or 2300 nm, could remove this lipid barrier in the area where the injection is to be made just prior to the injection to enhance the effectiveness thereof.

It is also known that the membranes walls of many cells are composed substantially of lipid and that these membranes differ somewhat from cell to cell. Radiation at one of the wavelengths indicated above may therefore be effective to selectively porate cells, the selectivity being achieved either as a result of controlling the focusing of the radiation to a targeted region and/or certain of the cells in the region porating at lower fluence or less time of radiation application than others as a result of cell size, wall thickness and/or other factors. Poration may be done for example to permit a drug or other therapeutic agent to enter the cell for healing or destruction thereof, for example, for the destruction of cancer cells, or to permit the content of the cell to flow out for various purposes. The poration may be temporary, or may be permanent resulting in cell destruction.

Finally, while in the discussion above the targeting of lipid as a chromophore for affecting hair removal in two different ways has been discussed, it is apparent that lipid could be targeted in other areas as a chromophore for the heating and either the destruction or therapy on other body components. Thus, in certain areas of the body, heating of lipid may be used to shrink collagen for wrinkle removal or skin toning or the lipid layer in the stratum corneum may be targeted for other purposes. Fat surrounding nerves, blood vessels or other biological structures may also be target for heating and treating the underlying structure. The radiation wavelength, intensity, and pulse duration would in each instance be adjusted based on the size of the lipid structure being targeted, its depth, the wavelength utilized, and other factors.

Figure 3:
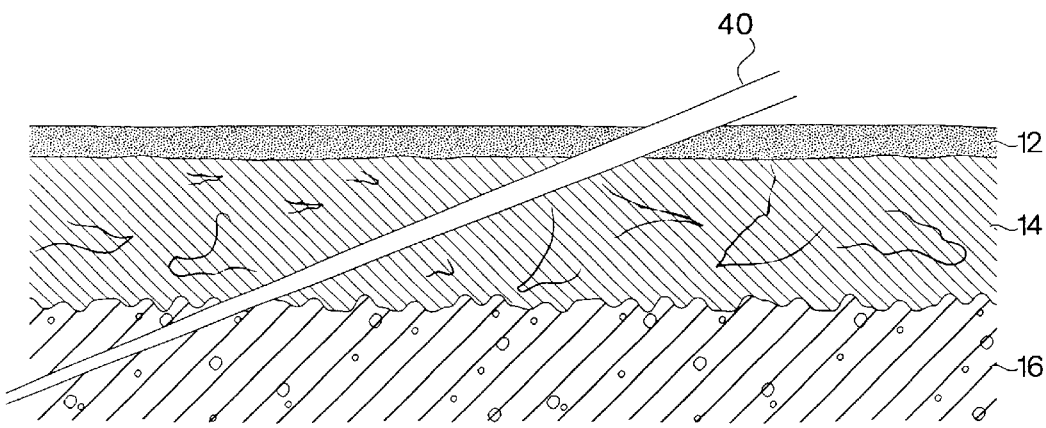
FIG. 3 is a sectional view illustrating a section of skin with subcutaneous fat under treatment employing another alternative embodiment of the invention.

FIG. 3 illustrates a technique which may be employed to treat subcutaneous fat either in areas where the dermis is too thick for treatment to be performed from the skin surface as shown in FIG. 2, where treatment is desired at depths in subcutaneous fat layer 16 which are too deep for treatment from the skin surface, where it is desired to operate at one of the more efficient longer wavelengths which do not normally penetrate to the subcutaneous fat, or for other reasons. In FIG. 3, a probe 40 is inserted through epidermis 12 and dermis 14 into subcutaneous fat region 16. Probe 40 may be a needle, or an opening may be formed in the skin through which a trocar or other cannula may be inserted, the probe 40 then passing through the cannula or trocar to the desired location. Other techniques known in the art for positioning a probe in subcutaneous fat region may be employed.

Probe 40 can contain an optical fiber or fiber bundle through which optical radiation at the wavelengths previously indicated may be applied to the end of the probe. The end of the probe may be formed to either direct the light straight ahead, to direct the light at some angle to the direction of the probe or to direct the radiation in more than one direction. Particularly where one of the longer wavelengths, for example 2300 nm, are utilized which have a high coefficient of absorption in fat, a dispersive lens might also be employed at the end of the needle to expend treatment area. A relatively large area of subcutaneous fat may be treated by a single insertion of the probe by moving the probe in and out of the subcutaneous fat and possibly by also rotating the probe about the entry point. Where light is coming out at an angle to the direction of the probe, the probe may also be rotated to cover a larger area. By inserting the probe at an angle as shown in FIG. 3, a larger area can be covered, though at a shallower depth. A smaller area to a greater depth can be covered by inserting probe 40 at a sharper angle. If the temperature to which the fat is raised by the radiations from the needle results in a liquid lipid pool being formed, a cannula could be included around the optical fiber in probe 40 to remove this liquid on a periodic or continuous basis, or the pool could be removed in the manner previously discussed. While the procedure of FIG. 3 may be used for any part of the body where fat is to be removed, it may be particularly advantageous for areas with smaller pockets of fat such as the face or neck. Further, while several techniques have been taught above for applying radiation within a preferentially absorbed wavelength band to subcutaneous fat for the treatment thereof, other techniques, including various surgical techniques, could be utilized for reaching selected regions of subcutaneous fat in appropriate situations.

Figure 4:
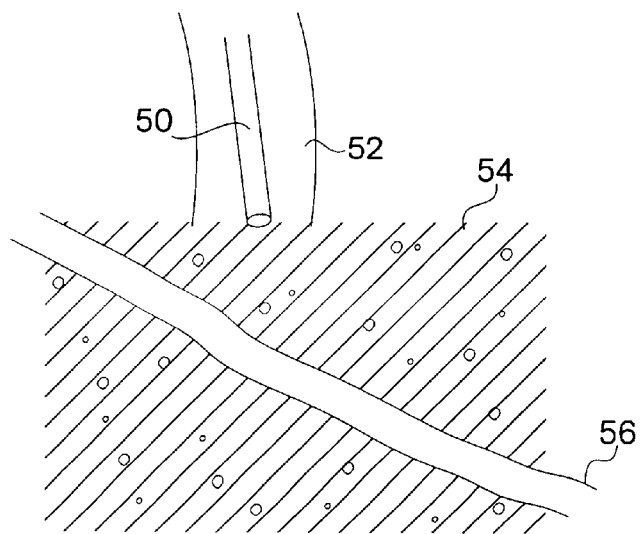
FIG. 4 is a sectional view illustrating a tool being utilized to clear fat from a vessel on which a surgical procedure is to be performed in accordance with the teachings of this invention.

Another area where the teachings of this invention might be advantageously employed is to remove fat covering vessels, organs, or other anatomical elements on which a surgical procedure is to be performed so that the surgical procedure may be more accurately and safely performed with better visibility. In this instance, the tool for removing the fat might be inserted through a surgical opening or might be part of an endoscope or other tool inserted through a body cavity. The tool inserted could be similar to probe 40 and, to minimize damage to surrounding tissue, is preferably placed in contact with the fat to be treated, or at least in near contact with such fat, for irradiation. Thus, in FIG. 4 the tool is shown as a probe 50 inserted through a catheter 52 to the fat 54 surrounding a vessel, gut or other vital structure 56 to be surgically treated. Catheter 52 could also include a standard probe to permit viewing of the area under treatment so that catheter 52 can be repositioned and treatment can be continued until a sufficient amount of the fat 54 has been removed to expose vessel 56. Where larger surgical incisions are made, the tool for removal/treatment of fat 54 from vessel 56 might be hand held by the surgeon and manipulated by him to remove fat. Since fat 54 preferentially absorbs radiation at the applied wavelengths, and strongly absorbs at the higher wavelengths usable where there is substantial contract between the probe and the fat to be treated, the treatment of fat 54 should result in little if any thermal damage to underlying vessel 56 and, particularly if the wavelength is at approximately 1715 nm, or 2300 nm, this danger will be significantly reduced from prior art procedures were the radiation utilized was not preferentially absorbed by the fat tissue. More specifically, the fluence and exposure duration can be adjusted to ablate or otherwise treat fat, but not the nearby or underlying non-fat tissue.

A technique has thus been disclosed for the targeting of lipid-rich or fat tissue to effect a desired treatment by the selective application of optical radiation to such fat tissue at a wavelength preferentially absorbed thereby. While for various embodiments, the fat tissue for targeting has been discussed above, including the sebaceous gland, subcutaneous fat and fat surrounding anatomical elements on which surgical procedures are to be performed, the invention is not limited to targeting only such fat tissue, but may be employed for the targeting of any lipid-rich tissue. Further, while specific hardware has been described for producing radiation within the selected wavelength bands, other radiation sources capable of producing radiation within such bands might also be utilized. Finally, while specific methods and hardware have been disclosed for applying the radiation to the various areas of lipid-rich tissue to be targeted, other techniques suitable for directing sufficient radiation at the requisite wavelengths to lipid-rich tissue may also be employed. Thus, while the invention has particularly been shown and described above with reference to preferred embodiments, the foregoing and other changes in form and detail may be made therein by those skilled in the art without departing from the spirit and scope of the invention, which invention is to be limited only by the following claims.

What is claimed is:

1. Apparatus for selectively targeting lipid-rich tissue to effect a desired treatment, said apparatus comprising:
   a source of radiation at a wavelength for which absorption coefficients for fat and water have a ratio which is at least 0.5, said source when energized, providing the radiation at a fluence and for a duration sufficient for the desired treatment; and
   a component which delivers the energy from said source to the lipid-rich tissue to be treated;
   wherein said wavelength is in a band 1700 to 1730 nm; and
   wherein said source is a potassium cadmium laser with a matrix $KCd(WO_4)_2$ which is doped with $Er^{3+}$ ions.

2. Apparatus as claimed in claim 1 wherein said ratio is at least 1.

3. Apparatus as claimed in claim 1 wherein the wavelength is in a band which is one of 900 nm to 930 nm, 1190 to 1220 nm, 1700 nm to 1730 nm, and 2280 nm to 2350 nm.

4. Apparatus as claimed in claim 1 wherein said fluence is approximately 0.5 J/cm² to 500 J/cm.

5. Apparatus as claimed in claim 1 wherein the component is an applicator adapted to be in pressure contact with skin above the lipid-rich tissue to be treated.

6. Apparatus as claimed in claim 1 wherein said energy is applied to the lipid-rich tissue to be treated through overlying skin, and wherein the component includes a mechanism which cools said overlying skin to a selected depth.

7. Apparatus as claimed in claim 1 wherein said component is a probe applied through skin overlying the lipid-rich tissue to be treated to a region containing such tissue.

8. Apparatus as claimed in claim 7 wherein said probe includes a cannula through which liquid fat formed as a result of the irradiation ablating lipid tissue walls is removed.

9. Apparatus as claimed in claim 1 including a cannula inserted into a pool of liquid fat formed as a result of the irradiation melting lipid tissue walls to remove the liquid fat.

10. Apparatus as claimed in claim 1 wherein said component is a tool which is adapted to be brought into at least near contact with lipid-rich tissue surrounding an anatomical element on which a surgical procedure is to be performed.

11. Apparatus as claimed in claim 1 wherein said fluence is approximately 0.5 J/cm² to 500 J/cm², depending on a number of factors including wavelength band utilized and size of the lipid-rich tissue being treated.

12. Apparatus as claimed in claim 1 wherein said duration is approximately 4 fs to several minutes.

13. Apparatus for selectively targeting lipid-rich tissue to effect a desired treatment, said apparatus comprising:
   a source of radiation at a wavelength for which absorption coefficients for fat and water have a ratio which is at least 0.5, said source when energized, providing the radiation at a fluence and for a duration sufficient for the desired treatment;
   a component which delivers the energy from said source to the lipid-rich tissue to be treated;
   a slotted head for irradiation delivery; and
   a mechanism for drawing a fold of skin to undergo said desired treatment into said slot of said head;
   wherein said wavelength is in a band which is one of (a) 880 to 935 nm, (b) 1160 to 1230 nm, (c) 1690 to 1780 nm, and (d) 2250 nm to 2450 nm.

14. A method for selectively targeting lipid-rich tissue to effect a desired treatment, said method comprising irradiating said lipid-rich tissue with optical radiation at a wavelength for which absorption coefficients for fat and water have a ratio which is at least 0.5, the radiation being at a fluence and for a duration sufficient for the desired treatment.

15. A method as in claim 14 wherein said ratio is at least 1.

16. A method as in claim 14 wherein said wavelength is in a band which is one of (a) 880 to 935 nm, (b) 1150 to 1230 nm, (c) 1690 to 1780 nm, and (d) 2250 nm to 2450 nm.

17. A method as claimed in claim 16 wherein the wavelength is in a band which is one of 900 nm to 930 nm, 1190 to 1220 nm, 1700 nm to 1730 nm, and 2280 nm to 2360 nm.

18. A method as claimed in claim 17 wherein said wavelength is one of approximately 920 nm, 1210 nm, 1715 nm, 2300 nm and 3375 nm.

19. A method as claimed in claim 16 wherein said fluence varies as a function of a number of factors including the wavelength band utilized and the size of the lipid-rich tissue being treated.

20. A method as claimed in claim 16 wherein said fluence is approximately 0.5 J/cm² to 500 J/cm².

21. A method as claimed in claim 16 wherein said duration is approximately 4 fs to several minutes.

22. A method as claimed in claim 16 wherein the lipid-rich tissue is at least one sebaceous gland.

23. A method as claimed in claim 22 wherein irradiating said tissue is performed by applying said energy to the skin surface overlying the at least one sebaceous gland.

24. A method as claimed in claim 23 wherein the wavelength is in one of band (b), (c), and (d).

25. A method as claimed in claim 16 wherein said lipid-rich tissue is subcutaneous fat.

26. A method as claimed in claim 25 wherein irradiating said tissue is performed by applying said energy to the skin surface overlying the subcutaneous fat to be treated.

27. A method as claimed in claim 26 wherein the wavelength is in one of band (a) and band (b).

28. A method as claimed in claim 26 wherein said energy is applied through an applicator applying pressure to skin above said subcutaneous fat to be treated.

29. A method as claimed in claim 26 including cooling the skin above the subcutaneous fat to be treated to a selected depth.

30. A method as claimed in claim 29 wherein said selected depth is in the dermal layer of said skin.

31. A method as claimed in claim 26 wherein a fold of skin containing subcutaneous fat to be treated is drawn into a slotted head and irradiated from at least two sides.

32. A method as claimed in claim 25 wherein irradiating said tissue is performed by applying said energy through a probe passed through the skin to the region of subcutaneous fat to be treated.

33. A method as claimed in claim 32 wherein said probe is passed into the subcutaneous fat at an angle to the skin surface, and including performing at least one of moving the probe in and out of the skin and rotating the probe about its skin entry point to irradiate and treat subcutaneous fat over a selected area.

34. A method as claimed in claim 32 including removing liquid fat formed as a result of the irradiation ablating lipid tissue walls through a cannula included as part of said probe.

35. A method as claimed in claim 25 wherein the radiation applied to said subcutaneous fat tissue is of sufficient fluence and duration to ablate walls of such tissue to form a liquid fat pool.

36. A method as claimed in claim 35 including inserting a needle into said pool, and removing liquid fat from said pool through said needle.

37. A method as claimed in claim 35 including said pool being absorbed into a patient's body.

38. A method as claimed in claim 35 including draining said pool through an opening in the patient's skin.

39. A method as claimed in claim 16 including focusing radiation to a treatment area in the subcutaneous fat.

40. A method as claimed in claim 35 wherein said fluence and duration are such that ablations of tissue walls occurs only to a selected depth in said subcutaneous layer.

41. A method as claimed in claim 16 wherein said lipid-rich tissue is fat surrounding an anatomical element on which a surgical procedure is to be performed, and wherein irradiating said tissue is performed by a tool in at least near contact with the fat to remove the fat from and thereby expose the element.

42. A method as claimed in claim 40 wherein said wavelength is in one of bands (b), (c), and (d).

43. A method as claimed in claim 16 wherein said treatment is achieved photomechanically, and wherein said duration is less than 1 $\mu$s.

44. A method as claimed in claim 16 wherein said lipid-rich tissue is heated to heat and treat tissue adjacent thereto.

45. A method as claimed in claim 44 wherein said lipid-rich tissue a sebaceous gland, heating of the sebaceous gland effecting hair removal.

46. A method as claimed in claim 45 wherein said lipid-rich tissue a subcutaneous fat, heating of the subcutaneous fat effecting hair removal.

47. A method as claimed in claim 16 wherein said lipid-rich tissues a cell membrane, heating of the cell membrane selectively porating the cell.

48. A method of treating lipid-rich tissue, comprising:
providing a radiation source;
projecting radiation from the radiation source onto a skin surface overlying the lipid-rich tissue, the entire radiation from the radiation source that is projected on the skin surface having a ratio of energy absorption by lipid tissue to energy absorption by water of at least 0.5; and
irradiating the lipid-rich tissue with a portion of the radiation.

49. The method of claim 48, wherein said ratio is greater than 1.5.

50. The method of claim 48, wherein the radiation is in a wavelength band which is at least one of (a) 1690 to 1780 nm, and (b) 2250 nm to 2450 nm.

51. The method of claim 50, wherein the radiation is in a wavelength band which is at least one of one of 1700 nm to 1730 nm, and 2280 nm to 2360 nm.

52. The method of claim 51, wherein the radiation has a wavelength approximately equal to at least one of 1715 nm, and 2300 nm.

53. The method of claim 50, wherein the radiation has a fluence in the range 15 J/cm$^2$ to 25 J/cm$^2$.

54. The method of claim 50, wherein the radiation has a duration in the range 10 ms to 100 ms.

55. The method of claim 50, wherein the lipid-rich tissue is at least one sebaceous gland.

56. The method of claim 50, wherein said lipid-rich tissue is subcutaneous fat.

57. The method of claim 56, wherein the radiation is applied through an applicator in contact with the skin surface, the method further comprising a step of applying pressure to the skin surface with the applicator.

58. The method of claim 56, further comprising a step of cooling the skin surface to cool to a selected depth.

59. The method of claim 58, wherein said selected depth is in the dermal layer.

60. The method of claim 56, further comprising a step of drawing a fold of skin containing the subcutaneous fat into a slotted bead, the irradiating occurring from at least two direction.

61. The method of claim 56, wherein the step of irradiating ablates the walls of the lipid-rich tissue to form a liquid fat pool.

62. The method of claim 61, further comprising a step of inserting a needle into said liquid fat pool, and removing liquid fat from said pool through said needle.

63. The method of claim 61, wherein said liquid fat pool is absorbed into a patient's body.

64. The method of claim 61, further comprising a step of draining said liquid fat pool through an opening in the skin surface.

65. The method of claim 56, further comprising a step of focusing the radiation to a treatment area in the subcutaneous fat.

66. The method of claim 50, wherein said lipid-rich tissue is heated to heat and treat tissue adjacent thereto.

67. The method of claim 66, wherein said lipid-rich tissue is a sebaceous gland, heating of the sebaceous gland effecting hair removal.

68. The method of claim 66, wherein said lipid-rich tissue is a subcutaneous fat, heating of the subcutaneous fat effecting hair removal.

69. The method of claim 50, wherein said lipid-rich tissues is a cell membrane, heating of the cell membrane pouting the cell.

70. The method of claim 48, wherein the radiation is at a wavelength for which a ratio of the absorption coefficient for fat and die absorption coefficient of water is at least 0.5.

71. The method of claim 70, wherein the wavelength is in a band 1700 to 1760 nm.

72. The method of claim 70, wherein the ratio is at least 2.5.

* * * * *

UNITED STATES PATENT AND TRADEMARK OFFICE
CERTIFICATE OF CORRECTION

| | |
|---|---|
| PATENT NO. | : 6,605,080 B1 |
| APPLICATION NO. | : 09/277307 |
| DATED | : August 12, 2003 |
| INVENTOR(S) | : Gregory B. Altshuler et al. |

It is certified that error appears in the above-identified patent and that said Letters Patent is hereby corrected as shown below:

Column 1, line 4, insert:

--FEDERALLY SPONSORED RESEARCH

This invention was made with Government support under Grant No. F49620-01-1-0014 awarded by the U.S. Department of the Air Force and Grant Nos. N00014-94-1-0927 and N00014-95-1-1265 awarded by the U.S. Department of the Navy. The Government has certain rights in this invention.--

Signed and Sealed this

Sixth Day of October, 2009

David J. Kappos
*Director of the United States Patent and Trademark Office*